United States Patent [19]

Temin et al.

[11] Patent Number: 5,124,263
[45] Date of Patent: Jun. 23, 1992

[54] RECOMBINATION RESISTANT RETROVIRAL HELPER CELL AND PRODUCTS PRODUCED THEREBY

[75] Inventors: Howard M. Temin; Joseph P. Dougherty, both of Madison, Wis.

[73] Assignee: Wisconsin Alumni Research Foundation, Madison, Wis.

[21] Appl. No.: 296,547

[22] Filed: Jan. 12, 1989

[51] Int. Cl.$^5$ ............................................. C12N 5/10
[52] U.S. Cl. .............................. 435/240.2; 435/320.1; 435/172.3; 435/236; 435/948; 935/32; 935/34; 935/57; 935/70; 935/71
[58] Field of Search ............... 435/240.2, 172.3, 69.1

[56] References Cited

U.S. PATENT DOCUMENTS 4,650,764  3/1987  Temin et al. ................... 435/240.2
4,861,719  8/1989  Miller ............................ 435/236

OTHER PUBLICATIONS

S. K. Chattopadhyay et al. (1981) J. Virology 39:777–791.
Markowitz, D. et al. (1988) Virology 167, 400–406.
J. Embretson et al.; 61 J. Virol. 3454–3462 (1987).
J. Embretson et al.; 61 J. Virol. 2675–2683 (1987).
J. Dougherty et al.; 84 P.N.A.S. USA 1197–1201 (1987).
H. Temin, *Retrovirus Vectors For Gene Transfer: Efficient Integration Into And Expression Of Exogenous DNA In Vertebrate Cell Genomes*, pp. 149–187, in Gene Transfer (Plenum Press 1986).
M. Emerman et al.; 14 Nuc. Acids Res. 9381–9396 (1986).
J. Dougherty et al.; 168 J. Mol. Cell. Bio. 4387–4395 (1986).
J. Embretson et al.; 60 J. Virol. 662–668 (1986).
K. Wilhelmsen et al.; 52 J. Virol. 172–182 (1984).
M. Emerman et al.; 50 J. Virol 42–49 (1984).
S. Watanabe et al.; 12 J. Mol. Cell. Bio. 2241–2249 (1983).
S. Watanabe et al.; 79 P.N.A.S. USA 5986–5990 (1982).
J. Wilson et al.; 85 P.N.A.S. USA 4421–4425 (1988).
D. Markowitz et al.; 62 J. Virol. 1120–1124 (1988).
B. Davis et al.; 314 Nature 550–553 (1985).
R. Bosselman et al.; 7 J. Mol. Cell. Bio. 1797–1806 (1987).
C. Gorman et al.; 79 P.N.A.S. USA 6777–6781 (1982).
M. Stinski et al.; 55 J. Virol. 431–441 (1985).
J. Sorge et al.; 4 J. Mol. Cell. Bio. 1730–1737 (1984).
A. Miller et al.; 6 J. Mol Cell. Bio. 2895–2902 (1986).
M. Eglitis et al.; 6 BioTechniques 608–614 (1988).
J. Knutson et al.; 164 Anal. Biochem. 44–52 (1987).
S. Kawai et al.; 4 J. Mol. Cell. Bio. 1172–1174 (1984).
P. Southern et al.; 1 J. Mol. App. Gen. 327–341 (1982).
R. Roberts; 15 Nuc. Acids Res. 189–217 (1987).
M. Wickens et al.; 226 Science 1045–1051 (1984).
C. Yanisch-Perron et al.; 33 Gene 103–119 (1985).

*Primary Examiner*—Richard A. Schwartz
*Assistant Examiner*—Johnny F. Railey, II
*Attorney, Agent, or Firm*—Quarles & Brady

[57] ABSTRACT

An improved helper cell for growing up stocks of replication incompetent retrovirus vectors is disclosed. The helper cell resists recombination events due to the fact that natural promoters and poly(A) sequences in the helper sequences have been replaced with foreign promoters and poly(A) sequences bearing little or no homology to the vectors. Plasmids containing these modified sequences can still create a helper cell with resulting expression of the needed helper proteins, yet there is much less risk of recombination events in the helper cell. Also disclosed are vectors produced by such helper cells, target cells infected by such vectors, and helper cells which convert vectors so that they can be used with hosts from different species.

6 Claims, 6 Drawing Sheets

FIG. 1
RETROVIRUS REPLICATION

FIG. 2
RETROVIRUS VIRION

RECOMBINATION RESISTANT RETROVIRAL HELPER CELL AND PRODUCTS PRODUCED THEREBY

This invention was made with United States government support awarded by NIH, Grant numbers: P01CA22443, T32CA09075, and P30CA07175. The United States Government has certain rights in this invention.

BACKGROUND OF THE INVENTION

A. Field Of The Invention

The present invention relates to recombinant DNA technology. It is especially useful in facilitating the introduction of foreign genes into eukaryotic cells.

B. Description Of The Art

There has been much interest in introducing foreign genes into eukaryotic cells. One reason for this interest is that some genetically caused diseases may be curable by introducing the foreign genes into the cells, and allowing the foreign genes to express a protein that the genetically defective cell cannot express. Another reason for this interest is that certain eukaryotic cells may prove to be the most suitable hosts for the production of certain eukaryotic proteins. Yet another reason is that this may permit farm animals to be genetically improved.

A promising approach for introducing foreign DNA into eukaryotic cells involves the use of retrovirus vectors. See J. Dougherty et al., 84 P.N.A.S. U.S.A. 1197-1201 (1987); M. Eglites et al., 6 BioTechniques 608-614 (1988). Retroviruses integrate into a target cell's chromosomes during their life cycle. By modifying the virus genome to include a gene of interest one has a means of carrying desired genes into the cell chromosomes. As a safety feature, the genetic material of the retrovirus vector is further modified so as to make it defective in virion structural proteins (e.g. gag, pol, env). This reduces the likelihood of the retrovirus replicating after integration in the target cell.

Helper (a.k.a. packaging) cell lines therefore had to be developed to permit the propagation of replication-defective retrovirus vectors. These cells operate by supplying proteins that the defective vector cannot supply for itself. Preferably, such helper cells are designed so as to produce the vectors without the presence of live helper viruses. See e.g. U.S. Pat. No. 4,650,764. In the U.S. Pat. No. 4,650,764 system, the helper sequences provide virion proteins (e.g. env, gag, pol) that the vectors have been designed not to have. The helper sequences are also defective (albeit in a different way, in encapsidation function).

A problem has arisen in using such helper cells. On occasion, spontaneous recombination in the helper cell of vector sequences with helper sequences leads to the formation of sequences that code for replication-competent retroviruses. One early attempt to reduce this recombination risk is described in U.S. Pat. No. 4,650,764. The reticuloendotheliosis virus gag-pol and env genes were positioned so as to be expressed from two separate segments. While this approach helped somewhat, this improvement alone was not sufficient to eliminate all problems.

Another problem with the use of helper cells was that they would not permit standard vectors to be efficiently used beyond a relatively limited host range.

Therefore, improved helper cells for use with retrovirus vectors are desired.

SUMMARY OF THE INVENTION

One embodiment of the present invention provides a helper cell. The cell has a retrovirus helper gene sequence which has a helper portion coding for a retrovirus virion protein for a specified retrovirus and which is capable of expressing the virion protein. A defective portion on the helper sequence renders the cell by itself unable to form the infectious virus which the first retrovirus helper gene sequence codes for. There is also a second retrovirus helped gene sequence in the cell having a defective helped portion which would have rendered the cell unable to form the infectious virus which the second retrovirus helped gene sequence codes for if suitable virion protein had not been supplied from expression of the first retrovirus helper portion or from another source. The second retrovirus helped gene sequence is a recombinant retrovirus sequence with a first part that is retrovirus and a second part that is a foreign gene protein coding part. The virion protein that is expressed by the first helper portion can permit the second retrovirus helped gene sequence to form infectious recombinant virus coding for the foreign gene.

The improvement relates to designing the helper cell such that no transcriptional promoter (and preferably no control signals) on the second helped sequence are present on the first helper sequence. In an especially preferred form, the 3' processing gene sequence(s) also different. A sequence would not be "present" if substantially mutated, replaced and/or deleted.

It is preferred that the control sequences on the two sequences have less than 35% sequence homology. One way to achieve this with respect to transcriptional promoters would be to have one transcriptional promoter be from one virus such as cytomegalovirus, and the other be from spleen necrosis virus.

In another preferred form, the helper cell can supply env protein from a virus whose primary natural host is from a first animal host (e.g. from one phylum), and the helped sequence can have a gene sequence coding for a retrovirus whose primary natural host is from a second animal host (e.g. from another phylum). This renders standard vectors able to efficiently infect animals of many different kinds.

Vectors produced by such cells and target cells infected with such vectors (and their progeny) are also provided.

It will be appreciated that the present invention provides helper cell sequences that are able to provide virion proteins of interest without the need for using transcription promoters or other non-coding sequences from a retrovirus. This significantly reduces the risks of nucleotide events since most such recombinations occur due to sequence homology between the vectors and the helper cell sequences. Also, the helper cells will be able to convert previously optimized vectors that were designed primarily for use in avian and murine host cells to vectors efficiently usable with a wide variety of other host cells (e.g. bovine).

The objects of the invention therefor include:

(a) providing helper cells, vectors, and hosts of the above kind;

(b) reducing recombination risks associated with using retroviral helper cells;

(c) reducing the risks of a helper cell producing replication competent virus; and (d) making known vectors useful with a broader range of hosts. There are still other objects and advantages of the invention that will be apparent from the description which follows.

DESCRIPTION OF THE PREFERRED EMBODIMENTS

A. Retrovirus Life Cycle

Figure 1:
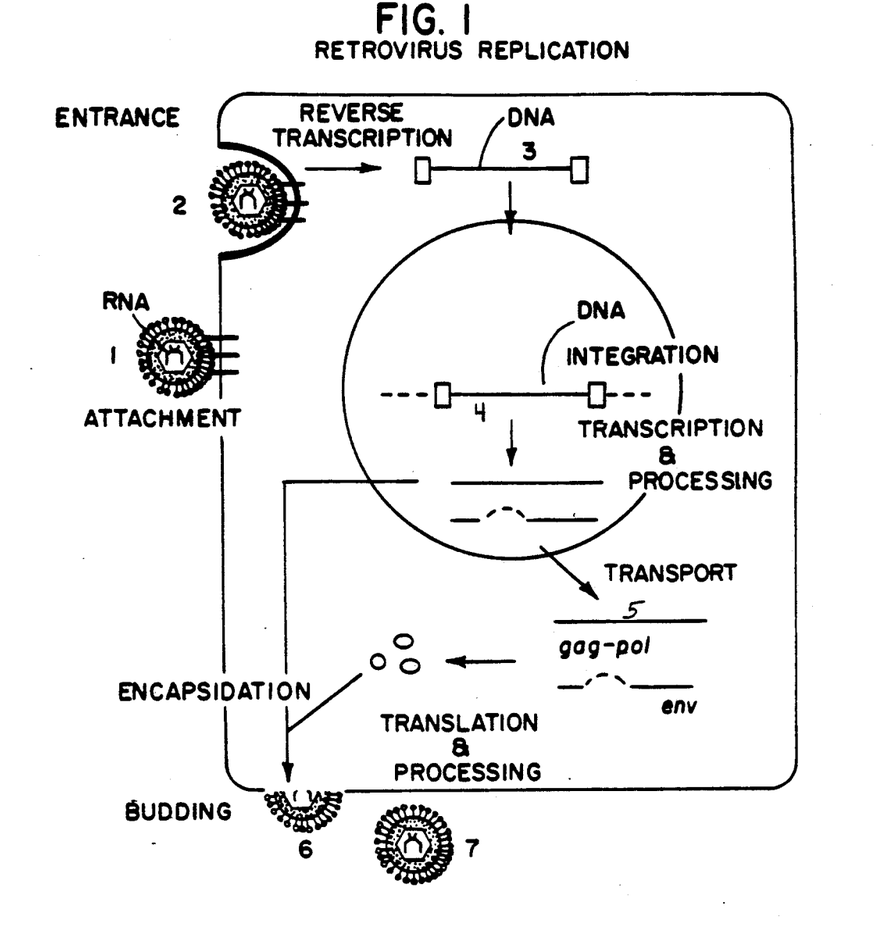
FIG. 1 depicts, in schematic form, the life cycle of a spleen necrosis virus.

The life cycle of a typical retrovirus is depicted in FIG. 1 of the drawings. The virus particle 1 carries the genetic message in RNA form. It attaches to the outer wall of a cellular host 2. After inserting itself into the cell, its RNA is reverse transcribed so as to form a DNA version 3 of the genetic sequence. The DNA then integrates into the cellular genome to form a "provirus" 4. Unless the viral genome has been altered so as to make the provirus replication defective, new virus particles 7 will then bud out of the cell after the provirus is transcribed to provide RNA, which then forms the virus protein 5 and structure 6.

Figure 2:
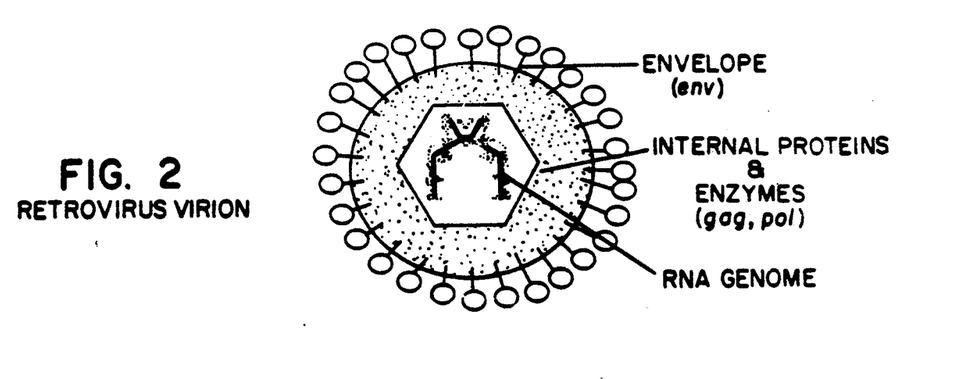
FIG. 2 shows the structure of a retroviral virion.

FIG. 2 depicts some of the details of a retrovirus virion, together with a depiction of where virion proteins from env, gag, and pol genes are used.

B. Basic Overview

We have constructed new helper cell lines. As was the case in U.S. Pat. No. 4,650,764, the gag-pol and the env genes are preferably expressed from two separate DNA helper sequences. In accordance with the present invention, the helper sequences can be constructed to have no nucleotide sequence homology to the sequences of the vector to be helped. This greatly reduces the risk of recombination.

Figure 3:
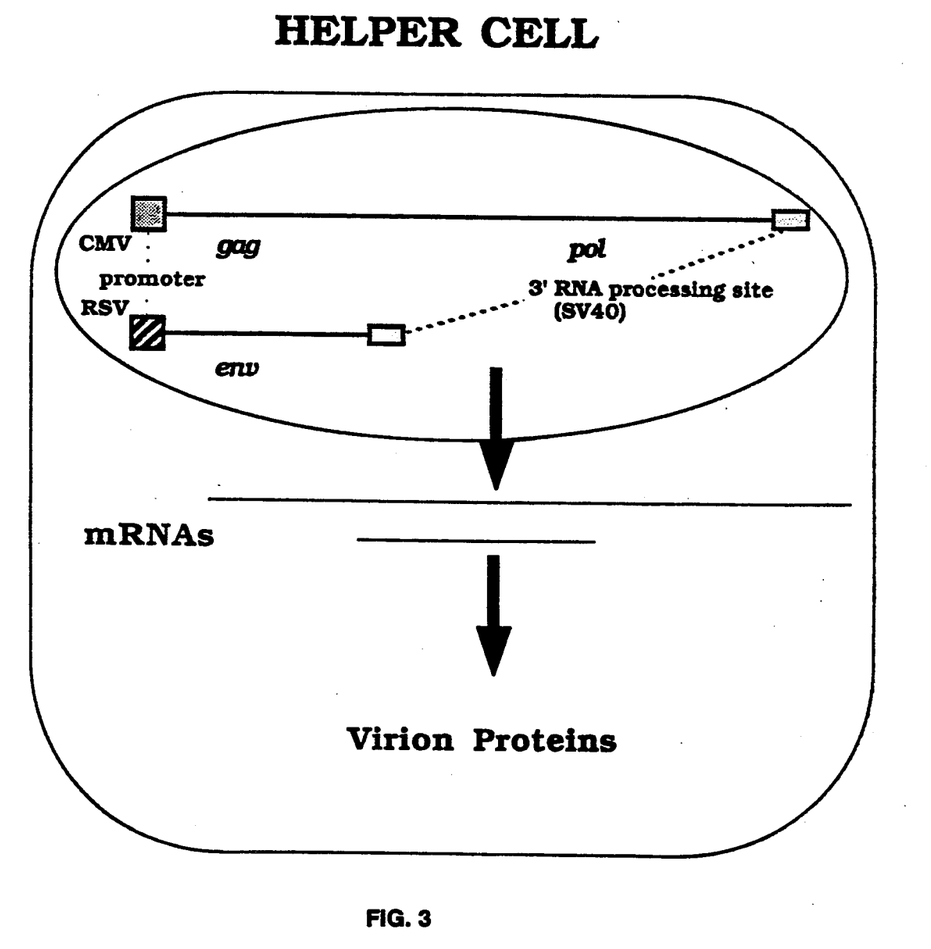
FIG. 3 schematically shows one helper cell of the present invention.

As shown in FIG. 3, retrovirus packaging cell lines have been created containing gag-pol genes from spleen necrosis virus which are expressed from a cytomegalovirus promoter and the SV40 polyadenylation sequences. The env gene from spleen necrosis virus is expressed from the Rous sarcoma virus promoter and the SV40 polyadenylation sequences. Although the SNV promoter and poly(A) sequences have been replaced with foreign promoters and poly(A) sequences, infection and expression functions are surprisingly retained.

As an alternative, invention also provides other helper cells containing the gag-pol genes from spleen necrosis virus expressed from a cytomegalovirus promoter and the SV40 polyadenylation sequences and the leukemia virus env gene from amphotropic murine leukemia virus expressed from a cytomegalovirus promoter and the SV40 polyadenylation sequences. In an especially preferred form, bovine leukemia virus env is expressed and used to package avian and murine retrovirus vectors.

C. Creation Of A gag-pol Source Plasmid

Intermediate pJDCMV19SV was constructed in two steps. First, the HindIII fragment containing the cytomegalovirus immediate early gene promoter isolated from pCATwt760 (see M. Stinski et al., 55 J. Virol. 431–441 (1985)) was inserted into the HindIII site of pUC19 (see Yanisch-Perron et al., 33 Gene 103–119 (1985); R. Roberts, 15 Nucl. Acids Res. Supp, r189-r217 (1987)) creating pJDCMV19. Second, the BamHI-HindIII fragment isolated from pSVL-141/+79 (see M. Wickens et al., 226 Science 1045–1051 (1984)) containing the SV40 late polyadenylation signal was inserted by blunt-ended ligation into the SmaI site of pJDCMV19, resulting in pJDCMV19SV.

Figure 4:
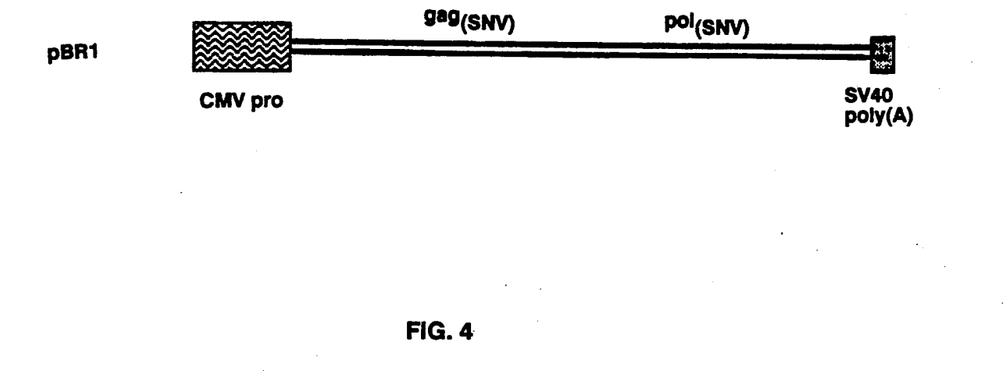
FIG. 4 schematically depicts plasmid pBR1, which contains coding sequences for gag and pol helper products.

Three steps were then required to make pBR1 (which expresses the gag-pol gene of SNV using the cytomegalovirus immediate early promoter and the SV40 polyadenylation sequence). First, the KpnI-BglII fragment from spleen necrosis virus (SNV) (DNA coordinates 3.5 to 6.629 kbp as specified in K. Wihelmsen et al., 52 J. Virol. 172–182 (1984)), was substituted for the KpnI-BglII fragment of pUC19 making pBRS. Second, the SNV KpnI fragment (DNA coordinates 0.676 to 3.5 kbp) was inserted into the KpnI site of pBRS resulting in pBRSNV. Third, the SalI fragment from pBRSNV containing the SNV gag-pol gene was cloned into the SalI site of pJDCMV19SV creating pBR1. FIG. 4 depicts Plasmid pBR1.

Figure 6:
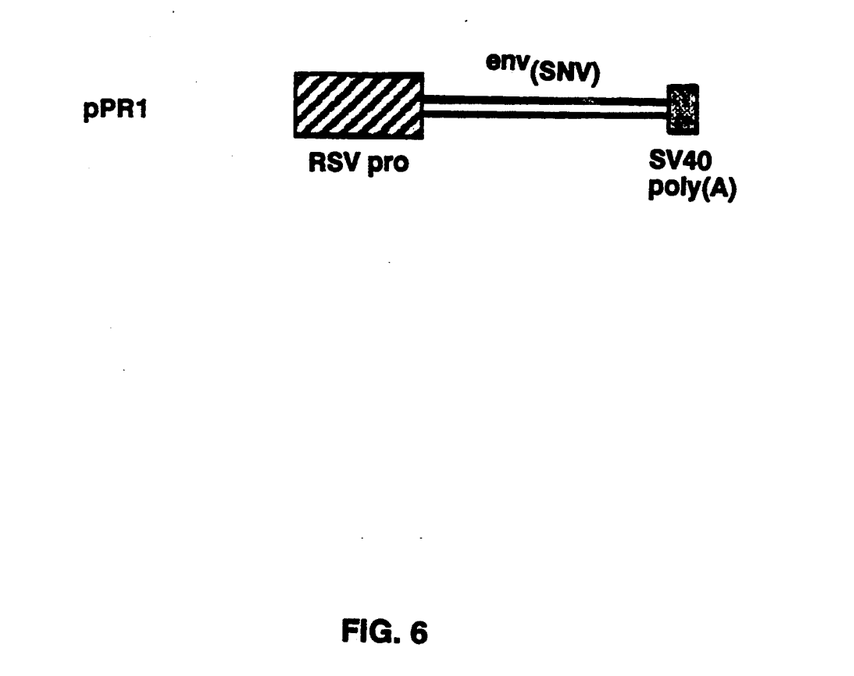
FIG. 6 schematically depicts plasmid pPR1, which contains a coding sequence for an env helper protein.

D. Creation Of An env Source Plasmid pPR1 expresses the env gene of SNV using the Rous sarcoma virus long terminal repeat promoter and the SV40 polyadenylation sequence. FIG. 6 depicts plasmid pBR1. It was constructed by replacing the HindIII-HpaI fragment of pRSVCAT (see C. Gorman et al., 79 P.N.A.S. U.S.A. 6777–6781 (1982)) with the HindIII-SacI fragment of SNV (DNA coordinates 5.653 to 7.747 kbp) by blunt-ended ligation.

Figure 7:
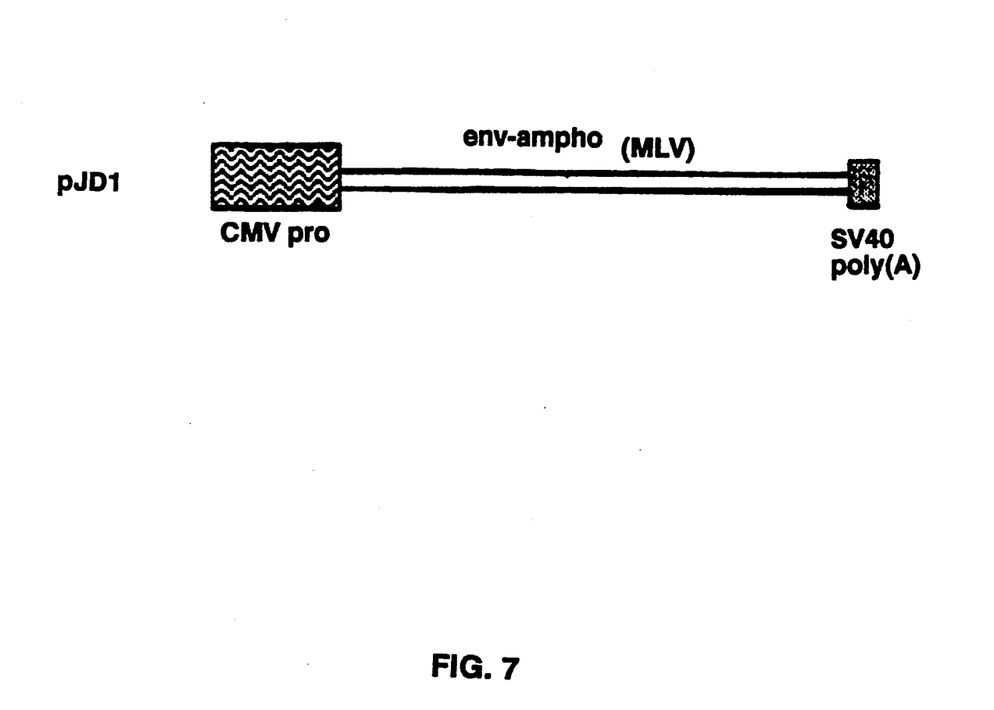
FIG. 7 schematically depicts plasmid pJD1, which contains a coding sequence for another env helper protein.

As an alternative, pJD1 expresses the env gene from amphotropic murine leukemia virus (MLV) strain 4070A using the cytomegalovirus immediate early promoter and the SV40 polyadenylation sequence. FIG. 7 depicts plasmid pJD1. It was made by inserting the SalI fragment from pTranspapp (see J. Sorge et al., 4 Mol. Cell Biol. 1730–1737 (1984)) containing the env gene from the amphotropic murine leukemia virus 4070A into the SalI site of pJDCMV19SV.

E. Helper Cells

Host chicken embryo fibroblasts (CEF) and D17 cells were grown as previously described (see S. Watanabe et al., 79 P.N.A.S. U.S.A. 5986–5990 (1982); M. Emerman et al., 50 J. Virol. 42–49 (1984)). The D17 cell line is an osteosarcoma-derived dog cell line which is permissive for SNV infection. To insert the protein source in the "helper" host D17, D17 cells, $4 \times 10^5$ in 60 mm petri dishes, were transfected with plasmids using either electroporation (see J. Knutson et al., 164 Anal. Biochem. 44–52 (1987)) or the DMSO/polybrene procedure (see S. Kawai et al., 4 Mol. Cell Biol. 1172–74 (1984)).

pSV2-neo ® is a marker that has previously been described in P. Southern et al., 1 J. Mol. Appl. Genet. 327-341 (1982). As a selection aid, D17 cells were transfected with this plasmid at the same time as they were infected with the two other plasmids. Transfected cells were selected with G418 antibiotic (Gibco) which is an antibiotic which will kill cells not containing the pSV2-neo ®. The surviving clones are very likely to have also picked up the pBR1 and pPR1. See generally U.S. Pat. No. 4,650,764.

The resulting selected colonies were grown up and screened for helper cell activity. Clones transfected with pBR1, pPR1, and pSV2neo were secured containing gag-pol and env genes from SNV and were designated "DSN" cells. Clones transfected with pBR1, pJD1, and pSV2neo were secured containing gag-pol genes from SNV and the env gene from amphotropic MLV and were designated "DAN" cells.

F. Production Of Vector Using Helper Cell

Figure 5:
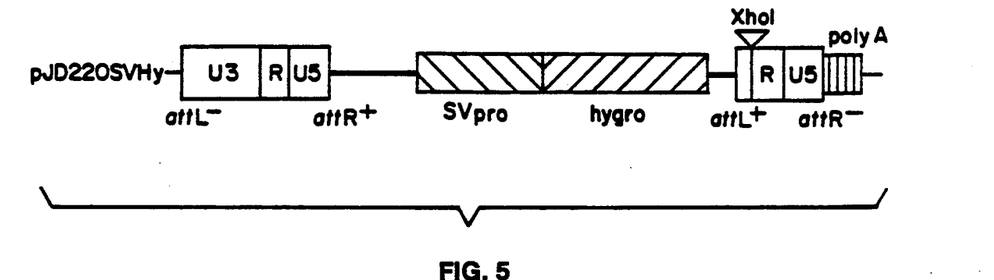
FIG. 5 shows pJD220SVHy, a vector to be "helped" in the helper cell.

JD220SVHy (see J. Dougherty et al., 84 P.N.A.S. 1197-1201 (1987)) is a preferred retroviral vector with a U3 deletion in the right hand LTR region (FIG. 5). Upon infection of sensitive target cells, this vector forms a provirus integrated in the cell genome albeit in provirus form both LTRs will have deleted U3 regions. Thus, a cell infected with this vector has much less chance of producing any virion produced from the provirus.

Conventional helper cells transfected with such vectors have in the past released modified vectors that do not have deleted LTRs. This indicated that the U3 deletion in the LTR had been restored prior to provirus formation by recombination events, since otherwise it would not have been possible to pass virus from the infected target cells. To lower the risk of homologous genetic interactions between the viral sequences in the helper cells and this preferred vector, the present invention provides helper cells with no nucleotide sequences homologous to the preferred vector.

Deposits of pJD220SVHy in D17 host dog cells and helper cell DSN have been made with the American Type Culture Collection, Rockville, Md., as ATCC Nos. 67393 and CRL9939 respectively. ATCC Nos. 67393 was deposited on Apr. 23, 1987. ATCC CRL 9939 was deposited on or before Jan. 11, 1989. Samples from the deposits will be made available in accordance with U.S. patent law requirements and the requirements of any applicable foreign patent laws. No patent license is intended by such availability.

As additional examples, the DAN (and DSN) cells were transfected with other vectors of interest (e.g. with pJD214Hy, J. Dougherty et al., 6 Mol. Cell Biol. 4387-4395 (1986)), and pAFVXMSVHy (see M. Emerman et al. 14 Nucl. Acids Res. 9381-9396 (1986)). Both vectors have a "foreign" hygromycin resistance gene. Thus, hygromycin-resistance cells can be selected after infection of the helper cell. Virus production using DSN cells followed procedures similar to those of (J. Embretsen et al., 60 J. Virol. 662-668 (1986); 61 J. Virol. 2675-2683 (1987); and 61 J. Virol. 3454-3462 (1987)).

G. Tests For Resistance To Recombination

In one experiment, at three and five weeks after transfection, virus was harvested from confluent helper cells and was used to infect fresh D17 cells. Five days after infection of these D17 cells, the supernatant media were assayed for DNA polymerase activity and none was found. The media were used to inoculate fresh D17 cells and chicken embryo fibroblasts. The fresh D17 cells were then selected for hygromycin-resistance. No resistant colonies were found. The media from the inoculated chicken embryo fibroblasts were, five days after inoculation, assayed for release of sedimentable DNA polymerase activity. No DNA polymerase activity was produced by the inoculated chicken embryo fibroblast cells.

In another test for the transfer of the packaging sequences, supernatant medium from DSN cells transfected with a vector was plated on D17 cells containing JD216Neo, and supernatant medium from these cells was used to inoculate fresh D17 cells which were selected for G418-resistance. None were found.

It will be appreciated that the present invention provides a means of supplying virion proteins (env, gag, pol) in a helper cell, with much less risk of infectious virus resulting. Surprisingly, a hybrid helper sequence that has a foreign transcriptional promoter will still permit the cell to be transfected and facilitate virion protein expression. Preferably, the foreign transcriptional promoter is from another virus, and preferably both LTRs on the helper sequences are modified (since retroviruses have a capacity to use a single sequence as template to create both ends at some points in their life cycle).

The invention is believed to be applicable to retroviruses other than just SNV, as well as to a wide range of foreign eukaryotic genes. While the invention does not remove all recombination risk (e.g. contaminated cells), it certainly greatly reduces the risk.

H. Cross Species Helper Cells

As indicated by the creation of pJD1, env fragments from other viruses (e.g. murine) can be inserted in plasmids like pJDCMV19SV and used with avian and murine vectors. This has also been extended to cover bovine leukemia virus env. We followed procedures analogous to those specified for murine leukemia virus env, isolated a known env sequence from bovine leukemia virus, inserted it into a helper sequence in place of avian virus env in a plasmid, and grew up vectors packaged in a helper cell with bovine leukemia virus env having avian virus internal coding.

The illustrative embodiments described above do not represent the full scope of the invention. Instead, the scope of the invention is to be judged by the claims which follow.

We claim:

1. In a helper cell of the type having:
   a host cell;
   a first retrovirus helper gene sequence in the cell which has a helper portion coding for a first retrovirus virion protein for a specified retrovirus and which has a first transcriptional promoter so as to be capable of expressing the first virion protein, and a defective encapsidation portion which assists in rendering the cell by itself unable to form the infectious value which the first retrovirus helper gene sequence codes for;
   a second retrovirus helper gene sequence in the cell which has a helper portion coding for a second retrovirus protein for the specified retrovirus and which has a second transcriptional promoter so as to be capable of expressing the second virion protein, the second helper gene sequence also having a defective encapsidation portion which together with the defective encapsidation portion of the first helper gene sequence renders the cell by itself unable to form the infectious virus which the second retrovirus helper gene sequence codes for;

a retrovirus helped gene sequence in the cell having a defective helped portion which would have rendered the cell unable to form the infectious virus which the retrovirus helped gene sequence codes for if suitable virion protein had not been supplied from expression of the first and second retrovirus helper portions or from another source; and said retrovirus helped gene sequence being a recombinant retrovirus sequence with a first part that is retrovirus and a second part that is a foreign gene protein coding part;

whereby the virion proteins expressed by the first and second helper portions can permit the retrovirus helped gene sequence to form infectious recombinant virus coding for the foreign gene; the improvement comprising:

no transcriptional promoter on the first or second helper sequence is present on the helped sequence and no transcriptional promoter on the first helper sequence is present on the second helper sequence.

2. The helper cell of claim 1, wherein no transcriptional promoter on the first or second helper sequence has more than 35% sequence homology to the sequence of any transcriptional promoter on the helped sequence.

3. The helper cell of claim 2, wherein no 3' processing sequence on the first or second helper gene sequence has the same sequence as any 3' processing sequence present on the helped gene sequence.

4. A recombinant retrovirus vector produced by the helper cell of claim 1.

5. A host cell transformed by the vector of claim 4.

6. A progeny cell of the host cell of claim 5.

* * * * *

UNITED STATES PATENT AND TRADEMARK OFFICE
CERTIFICATE OF CORRECTION

PATENT NO. : 5,124,263
DATED : June 23, 1992
INVENTOR(S) : Howard M. Temin; Joseph P. Dougherty It is certified that error appears in the above-identified patent and that said Letters Patent is hereby corrected as shown below:

Column 3, Lines 15 and 16     "gag and pol helper products" should be --gag and pol helper proteins--

Column 3, Line 20     "env" should read --env--

Column 3, Line 23     "env" should read --env--

Column 6, Line 61     "value" should read --virus--

Signed and Sealed this

Third Day of August, 1993

Attest:

MICHAEL K. KIRK

Attesting Officer     Acting Commissioner of Patents and Trademarks